(12) United States Patent
Goebbel et al.

(10) Patent No.: US 7,973,183 B2
(45) Date of Patent: Jul. 5, 2011

(54) PROCESS FOR THE PREPARATION OF AN OLEFIN OXIDE

(75) Inventors: Hans-Georg Goebbel, Kalmthout-Nieuwmoer (BE); Peter Bassler, Viernheim (DE); Joaquim Henrique Teles, Otterstadt (DE); Peter Rudolf, Ladenburg (DE); Ulrich Mueller, Neustadt (DE); Anna Forlin, Vigonza (IT); Malte Schulz, Hollern-Tw. (DE); Meinolf Weidenbach, Drochtersen (DE)

(73) Assignees: BASF SF, Ludwigshafen (DE); The Dow Chemical, Midland, MI (US)

(*) Notice: Subject to any disclaimer, the term of this patent is extended or adjusted under 35 U.S.C. 154(b) by 50 days.

(21) Appl. No.: 12/599,395

(22) PCT Filed: Apr. 24, 2008

(86) PCT No.: PCT/EP2008/054973
§ 371 (c)(1),
(2), (4) Date: Nov. 9, 2009

(87) PCT Pub. No.: WO2008/135398
PCT Pub. Date: Nov. 13, 2008

(65) Prior Publication Data
US 2010/0305369 A1 Dec. 2, 2010

Related U.S. Application Data

(60) Provisional application No. 60/947,834, filed on Jul. 3, 2007.

(30) Foreign Application Priority Data

May 8, 2007 (IT) .............................. MI2007A0932

(51) Int. Cl.
*C07D 301/12* (2006.01)
(52) U.S. Cl. ...................................................... 549/531
(58) Field of Classification Search .................... 549/531
See application file for complete search history.

(56) References Cited

U.S. PATENT DOCUMENTS

| | | | |
|---|---|---|---|
| 5,397,475 A | 3/1995 | Millar et al. | |
| 5,760,253 A | 6/1998 | Danner et al. | |
| 5,840,933 A | 11/1998 | Jubin, Jr. et al. | |
| 5,849,937 A | 12/1998 | Jubin, Jr. et al. | |
| 5,912,367 A | 6/1999 | Chang | |
| 5,932,187 A | 8/1999 | Ledon et al. | |
| 6,380,119 B1 | 4/2002 | Grosch et al. | |
| 6,727,371 B2 * | 4/2004 | Muller et al. | 549/531 |
| 7,863,468 B2 * | 1/2011 | Schindler et al. | 549/533 |
| 2003/0050487 A1 | 3/2003 | Muller et al. | |
| 2003/0162983 A1 | 8/2003 | Strebelle et al. | |

FOREIGN PATENT DOCUMENTS

| | | |
|---|---|---|
| DE | 42 22 109 | 1/1994 |
| DE | 10 2004 003 003 | 9/2005 |
| EP | 0 200 260 | 12/1986 |
| EP | 0 311 983 | 4/1989 |
| EP | 0 405 978 | 1/1991 |
| EP | 1 122 249 | 8/2001 |
| EP | 1 403 259 | 3/2004 |
| WO | 98 55228 | 12/1998 |
| WO | 01 72729 | 10/2001 |
| WO | 02 085873 | 10/2002 |
| WO | 02 085874 | 10/2002 |
| WO | 2005 068062 | 7/2005 |
| WO | 2006 108748 | 10/2006 |

OTHER PUBLICATIONS

Meier, W.M. et al., "Atlas Of Zeolite Framework Types", Elsevier, 5th edition, pp. 202-203, (2001).
"Ullmann's Encyclopedia of Industrial Chemistry", Fifth edition, Volme A13: High-Performance Fibers to Imidazole and Derivatives, pp. 447-461, (1989).

* cited by examiner

*Primary Examiner* — Sikarl A Witherspoon
(74) *Attorney, Agent, or Firm* — Oblon, Spivak, McClelland, Maier & Neustadt, L.L.P.

(57) ABSTRACT

The present invention relates to a continuous process for the preparation of an olefin oxide wherein an olefin is reacted with a hydroperoxidein the presence of a catalyst, and wherein the reaction which is carried out in at least three reactors operated in parallel is controlled by specifically adjusting the catalyst loads in the reactors.

20 Claims, No Drawings

US 7,973,183 B2

PROCESS FOR THE PREPARATION OF AN OLEFIN OXIDE

FIELD OF THE INVENTION

The present invention relates to a continuous process for the preparation of an olefin oxide comprising a stage (a) wherein an olefin is reacted with a hydroperoxide in the presence of a catalyst, preferably a zeolite catalyst. Still more preferably, this reaction is carried out in the presence of a suitable solvent or solvent mixture. This stage (a) of the continuous process comprises at least one a stage (i) wherein
(1) the reaction is carried out in at least 3 reactors R1, R2, . . . Rn connected in parallel, wherein each reactor contains the catalyst and wherein the standard catalyst load LS of a given reactor deviates not more than ±5% from the average standard catalyst load LSA;
(2) at any given point in time during carrying out the reaction, at least one of the at least 3 reactors R1, R2, . . . Rn is out of operation for regenerating the catalyst present in this at least one reactor so that at least 2 reactors remain in operation;
(3) at this point in time, the at least 2 reactors in operation are operated so that
   (3.1) the average catalyst load LA is in the range of from (0.8-1.2) LSA;
   (3.2) the catalyst load L of a given reactor is within the range of (0.5-1.5) LS, LS being the standard catalyst load of this reactor;
   (3.3) the catalyst load L of at least one of these reactors deviates more than ±5% from the average standard catalyst load LSA and is different from the catalyst load of each of the other reactors.

BACKGROUND OF THE INVENTION

In numerous chemical processes catalysts are used which loose activity during the process and therefore lower yields are obtained. Generally, these catalysts have to be regenerated. As a result, the reactor or the reactors containing the catalyst has/have to be taken out of operation. Therefore, several publications are concerned with improvement of these processes.

WO 01/72729 and U.S. Pat. No. 6,727,371 B2 disclose a continuous process for reacting an organic compound with hydroperoxide in the presence of a catalyst, wherein the reaction is carried out in a reactor assembly comprising at least two reactors connected in parallel. One of the reactors can be taken out of operation to allow for regeneration of the catalyst whereas the other reactor is still operated to allow for a continuous process.

DE 10 2004 003 003.0 relates to a process for the continuous preparation of a chemical compound, in which a specially designed shell-and-tube reactor is used in at least one reactor used for the preparation of this compound. The use of two or more reactors connected in parallel is also disclosed.

WO 02/085873 discloses a process for the catalytic epoxidation of olefins with hydrogen peroxide in a continuous flow reaction system, wherein the reaction mixture is passed through a fixed catalyst bed in down-flow operation mode and the reaction heat is at least partially removed during the course of the reaction. The use of two or more reactors connected in parallel is also disclosed.

WO 02/085874 relates to a process for the catalytic epoxidation of olefins with hydrogen peroxide in a multiphase reaction mixture which can be conducted in several reactors connected in series or in parallel.

EP 1 403 259 A1 relates to a continuous process for the epoxidation of olefins using a heterogeneous catalyst for promoting the epoxidation reaction, whereby deactivation of the catalyst has been considerably reduced. The use of two or more reactors connected in parallel is also disclosed.

U.S. Pat. No. 5,760,253 and U.S. Pat. No. 5,840,933 relate to a reactor and a process for the production of oxirane compounds by reaction of an olefin such as propylene with an organic hydroperoxide using a solid contact catalyst, wherein the reactor is divided into a series of separate zones, each zone containing a bed of solid epoxidation catalyst. The use of reactors connected in parallel is not disclosed.

According to U.S. Pat. No. 5,912,367, propylene is converted to propylene oxide in a highly efficient liquid phase process wherein temperature and pressure are both increased over the course of the epoxidation, which is preferably conducted in a continuous mode of operation. The catalyst used is a heterogeneous catalyst such as titanium silicalite or titania-on-silica. The oxidizing agent is an active oxygen species such as hydrogen peroxide or an organic hydroperoxide. When the desired yield of propylene oxide can no longer be maintained, the catalyst is replaced or regenerated.

U.S. Pat. No. 5,849,937 discloses an olefin epoxidation process using a plurality of reactor vessels, each containing a fixed bed of a heterogeneous catalyst such as titania-on-silica. The reactor vessels are connected in series whereby a feed-stream comprised of olefin and an active oxygen species is passed through said series of reactor vessels in contact with the heterogeneous catalyst to accomplish conversion of the olefin to the corresponding epoxide. As the activity of the catalyst in an individual reactor vessel falls to an undesirably low level, said reactor vessel is taken out of service and a replacement reactor vessel containing fresh or regenerated catalyst introduced. The replacement reactor vessel may, in alternative embodiments of the process, be the first or the last reactor vessel in said series. For example, the feedstream may first be contacted with either the most active or the least active charge of catalyst within the series of reactor vessels. The use of reactors connected in parallel is not disclosed.

Since the deactivation of the catalyst is believed to be a continuous process, the processes as disclosed in the state of the art still have losses in yield of the desired reaction product over the reaction time.

It is an objective of the present invention to provide a novel process for the preparation of an olefin oxide which is advantageous with respect to the overall yield in reaction product compared with state-of-the-art processes.

SUMMARY OF THE INVENTION

The present invention relates to a continuous process for the preparation of an olefin oxide comprising a stage (a)
(a) reacting an olefin with a hydroperoxide in the presence of a catalyst to obtain a mixture (Ma) comprising olefin oxide, wherein stage (a) comprises at least one reaction stage (i) wherein in (i)
(1) the reaction is carried out in at least 3 reactors R1, R2, . . . Rn connected in parallel, wherein each reactor contains the catalyst and wherein the standard catalyst load LS of a given reactor deviates not more than ±5% from the average standard catalyst load LSA;
(2) at any given point in time during carrying out the reaction, at least one of the at least 3 reactors R1, R2, . . . Rn is out of operation for regenerating the catalyst present in this at least one reactor so that at least 2 reactors remain in operation;

(3) at this point in time, the at least 2 reactors in operation are operated so that
  (3.1) the average catalyst load LA is in the range of from (0.8-1.2) LSA;
  (3.2) the catalyst load L of a given reactor is within the range of (0.5-1.5) LS, LS being the standard catalyst load of this reactor;
  (3.3) the catalyst load L of at least one of these reactors deviates more than ±5% from the average standard catalyst load LSA and is different from the catalyst load of each of the other reactors;
wherein the catalyst load L of a given reactor is the molar amount of hydroperoxide fed per kilogram catalyst and per hour into this reactor;
wherein the standard catalyst load LS of a given reactor is the catalyst load which, if constantly applied for a given reaction period T to this reactor containing the catalyst, results in the maximum yield of olefin oxide based on hydroperoxide;
wherein the average standard catalyst load LSA is the sum of the standard catalyst loads of all reactors R1, R2, . . . Rn divided by n;
and wherein the average catalyst load LA at a given point in time is the sum of the catalyst loads of the reactors in operation at this point in time divided by the number of these reactors.

DETAILED DESCRIPTION OF THE INVENTION

According to the process of the present invention, stage (i) is carried out in at least 3 reactors R1, R2, . . . Rn which are connected in parallel. The term "connected in parallel" as used in this context relates to an apparatus set-up which comprises suitable means for distributing at least one feed stream to be introduced into stage (i) to the reactors R1, R2, . . . Rn by dividing this feed stream into n substreams and by introducing each substream into an individual reactor.

As far as the reactors used in stage (i) of the present invention are concerned, generally no limitations exist.

The epoxidation reaction is carried out in the presence of a catalyst suitable for catalyzing the reaction of the olefin with the hydroperoxide. While there are no specific restrictions, zeolite catalysts are preferred. Zeolites are, as is known, crystalline aluminosilicates having ordered channel and cage structures and containing micropores. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001.

Zeolites in which no aluminium is present and in which part of the Si(IV) in the silicate lattice is replaced by titanium as Ti(IV) are also known. These titanium zeolites, in particular those having a crystal structure of the MFI type, and possible ways of preparing them are described, for example, in EP 0 311 983 A2 or EP 0 405 978 A1. Apart from silicon and titanium, such materials can further comprise additional elements such as aluminium, zirconium, tin, iron, cobalt, nickel, gallium, germanium, boron or small amounts of fluorine. In the zeolite catalysts, at least a portion of the titanium of the zeolite can be replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, in particular those having a crystal structure of the MFI type, and possible ways of preparing them are described, for example, in WO 98/55228, EP 0 311 983 A2, EP 0 405 978 A1, or EP 0 200 260 A2.

It is known that titanium zeolites having the MFI structure can be identified via a particular X-ray diffraction pattern and also via a lattice vibration band in the infrared (IR) region at about 960 $cm^{-1}$ and thus differ from alkali metal titanates or crystalline and amorphous $TiO_2$ phases.

Specific mention may be made of titanium-, germanium-, tellurium-, vanadium-, chromium-, niobium-, zirconium-containing zeolites having a pentasil zeolite structure, in particular the types which can be assigned X-ray-crystallographically to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MFI, MFS, MON, MOR, MSO, MTF, MTN, MTT, MTW, MWW, NAB, NAT, NES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YNU, YUG and ZON, and also mixed structures of two or more of the abovementioned structures. Furthermore, titanium-containing zeolites having the ITQ-4, SSZ-24, TTM-1, UTD-1, CIT-1 or CIT-5 structure are also conceivable for use in the process of the invention. Further titanium-containing zeolites which may be mentioned are those having the ZSM-48 or ZSM-12 structure.

For the purposes of the present invention, preference is given to using Ti zeolites having an MFI structure, an MEL structure, an MFI/MEL mixed structure or an MWW structure. Further preference is given specifically to the Ti-containing zeolite catalysts which are generally referred to as "TS-1", "TS-2", TS-3", and also Ti zeolites having a framework structure isomorphous with beta-zeolite. Very particular preference is given to using zeolite catalysts of the TS-1 structure and the Ti-MWW structure. The abbreviation "TS" stands for "titanium silicalite".

The catalysts, especially preferably the titanium zeolite catalysts and still more preferably the catalysts having TS-1 or Ti-MWW structure, can be employed as powder, as granules, as microspheres, as shaped bodies having, for example, the shape of pellets, cylinders, wheels, stars, spheres, honeycombs and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm. In order to increase the bulk density of the extrudates in the reactor, it is preferred to cut the extrudates with a stream essentially consisting of an inert gas.

According to a preferred embodiment, a TS-1 or Ti-MWW catalyst is employed according to the present invention which is produced by first forming microspheres, for example microspheres formed according to EP 0 200 260 A2, and then forming said microspheres to obtain shaped bodies, preferably extrudates as described above, using, e.g., at least one suitable binder in a suitable amount.

According to especially preferred embodiments of the present invention, extrudates as defined above are employed as catalyst particles, wherein at least 99 wt.-% of the extrudates are comprised of catalytically active material, preferably TS-1 or Ti-MWW, and inert binder material, preferably silicon dioxide. According to even more preferred embodiments, the weight ratio of catalytically active material to silicon dioxide is in the range of from 1.5:1-4.5:1, more preferably of from 2.0:1-4.0:1, and even more preferably of from 2.5:1-3.5:1.

Therefore, the reactions in stage (i) are preferably carried out in suspension mode, fluidized-bed mode or fixed-bed mode, most preferably in fixed-bed mode.

Generally, the reaction mixture can be passed through the reactors in stage (i) in up-flow mode or in downflow mode.

In case the reactors are operated in downflow mode, it is preferred to use fixed-bed reactors which are preferably tubular, multi-tubular or multi-plate reactors, most preferably equipped with at least one cooling jacket. In case of downflow operation of the reactors, it is possible to choose the reaction conditions such that the reaction is carried out in a single phase, more preferably in a single liquid phase, or in a multiphase system comprising, for example, 2 or 3 phases such as at least two liquid phases or at least one liquid phase and at least one gas phase. According to the present invention, it is also possible to operate the reaction in a trickle bed mode.

In case the reactors are operated in upflow mode, it is preferred to use fixed-bed reactors. According to this embodiment, it is preferred to conduct the reaction so that one single liquid phase is present. In case the reactors are operated in upflow mode, the reactors connected in parallel in stage (i) are particularly preferably tube reactors, multi-tube reactors or multi-plate reactors, more preferably multi-tube reactors and especially preferably shell-and-tube reactors comprising a multitude of tubes such as from 1 to 20,000, preferably from 10 to 10,000, more preferably from 100 to 8,000, more preferably from 1,000 to 7,000 and particularly preferably from 3,000 to 7,000 tubes.

In order to remove heat generated during the epoxidation reaction at least partially, it is preferred to equip the reactors used in stage (i) with suitable cooling means such as a cooling jacket. As cooling medium used for cooling the reaction media in above-mentioned reactors equipped with cooling jackets, there are no specific restrictions. Especially preferred are oils, alcohols, liquid salts or water, such as river water, brackish water and/or sea water, which can in each case, for example, preferably be taken from a river and/or lake and/or sea close to the chemical plant in which the process of the invention is carried out and, after any necessary suitable removal of suspended material by filtration and/or sedimentation, be used directly without further treatment for cooling the reactors. Secondary cooling water which is preferably conveyed around a closed circuit is particularly useful for cooling purposes. This secondary cooling water is generally essentially deionized or demineralised water to which at least one antifouling agent has preferably been added. More preferably, this secondary cooling water circulates in a closed loop between the reactor of the invention and, for example, a cooling tower. Preference is likewise given to the secondary cooling water being, for example, countercooled in at least one countercurrent heat exchanger by, for example, river water, brackish water and/or sea water.

Therefore, the present invention also relates to a process as described above wherein in stage (i), at least three shell-and-tube reactors each having of from 1 to 20,000 internal tubes and being continuously operated in upflow mode, said reactors being operated in parallel, are employed. Still more preferably, the reaction in the at least three reactors of stage (i) is conducted so that in the respective reactor, a single liquid phase is present. Even more preferably, in each of the reactors used in stages (i) and (iii), the catalyst used for the epoxidation reaction is employed as fixed-bed reactor wherein the catalyst is a titanium zeolite catalyst, more preferably a TS-1 or Ti-MWW catalyst.

According to a preferred embodiment, the epoxidation reaction in the at least 3 reactors of stage (i) is carried out in a solvent.

As to the solvent used in stage (i), there are no specific restrictions. For example, water, alcohols, preferably lower alcohols, further preferably alcohols having less than 6 carbon atoms, for example methanol, ethanol, propanols, butanols and pentanols, diols or polyols, preferably those having less than 6 carbon atoms, ethers, for example diethyl ether, tetrahydrofuran, dioxane, 1,2-diethoxyethane and 2-methoxyethanol, esters, for example methyl acetate or butyrolactone, amides, for example dimethylformamide, dimethylacetamide and N-methylpyrrolidone, ketones, for example acetone, nitriles, for example acetonitrile, or mixtures of two or more of the above-mentioned compounds can be used in general. In case a TS-1 catalyst is used according to the present invention, methanol and/or acetonitrile, optionally as mixture with water, is/are preferred, methanol being especially preferred. In case a Ti-MWW catalyst is used according to the present invention, methanol and/or acetonitrile, optionally as mixture with water, is/re preferred, acetonitrile being especially preferred.

As to the olefin reacted in stage (a) with hydroperoxide, there are no specific restrictions. For example, ethene, propylene, 1-butene, 2-butene, isobutene, butadiene, pentenes, piperylene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprene, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils can be reacted with hydrogen peroxide.

Preference is given to using alkenes containing from 2 to 8 carbon atoms. Particular preference is given to reacting ethene, propene and butene. Very particular preference is given to reacting propylene.

In the context of the present invention, it is possible to introduce propene as chemical grade propene in which propane is present in a volume ratio of propene to propane of from about 97:3 to about 95:5. It is also possible to introduce propene as refinery grade propene. In case refinery grade propene is used, the mixture contains preferably 50 to 85 vol.-%, more preferably 55 to 80 vol.-%, in particular 60 to 75 vol.-% propene, the remaining part being propane, and can additionally contain traces of C2 and C4 compounds. Preferably, according to the present invention polymer grade propene is used which preferably contains at least 99.0 vol.-% of propene, more preferably at least 99.2 vol.-% of propene, in particular at least 99.5 vol.-% of propene.

In the context of the present invention it is also possible to bring the propene into contact with an absorber bed prior to introducing it into the reactors R1, R2, . . . , Rn and, as described as preferred embodiment below, into the at least one reactor of stage (iii). According to this embodiment, it was found that the life time of the catalyst used for the epoxidation can be increased. Preferably, according to this embodiment, the amount of impurities in the propene feed such as for example traces of sulphur, arsenic or phosphorous can be reduced. In general, the absorber bed contains a catalyst. Catalysts suitable for this purpose are generally known to the person skilled in the art. Suitable catalysts for the absorber bed are for example catalysts comprising aluminium oxide, particularly aluminium oxide in combination with at least one further oxide such as copper oxide or zinc oxide. The absorber bed can for example comprise a catalyst such as Puristar® R3-12 and Selexsorb® COS as an absorber. The surface area of the catalysts for the absorber bed is generally in the range of 100 to 500 m$^2$/g, for example 100 to 280 m$^2$/g, preferably 100 to 150 m$^2$/g. The operating temperature of the absorber bed generally is in the range of from 15 to 50° C. The flow rate through the absorber bed as empty tube velocity is generally in the range of from 0.1 to 10 cm/s, more preferably in the range of from 0.5 to 8 cm/s, in particular in the range of from 1.0 to 5.0 cm/s. The contact load of the absorber is generally in the range of from 1 to 10 kg(propene)/kg(contact)/h, preferably in the range of from 3 to 6 kg(propene)/kg(contact)/h. The absorber can be operated in downflow mode or in upflow mode, the downflow mode being preferred.

The hydroperoxide, preferably hydrogen peroxide is used in the process according to the invention in the form of an aqueous solution with a hydroperoxide, preferably hydrogen peroxide content of generally of from 1 to 90 wt.-%, preferably of from 10 to 70 wt.-%, more preferably from 10 to 60 wt.-%. A solution having of from 20 to less than 50 wt.-% of hydroperoxide, preferably hydrogen peroxide is particularly preferred.

According to another embodiment of the present invention, a crude aqueous hydrogen peroxide solution can be employed. As crude aqueous hydrogen peroxide solution, a solution can be used which is obtained by extraction of a mixture with essentially pure water wherein the mixture results from a process known as anthrachinone process (see, e.g., Ullmann's Encyclopedia of Industrial Chemistry, 5th edition, volume 13 (1989) pages 447-457). In this process, the hydrogen peroxide formed is generally separated by extraction from the working solution. This extraction can be performed with essentially pure water, and the crude aqueous hydrogen peroxide is obtained. According to one embodiment of the present invention, this crude solution can be employed without further purification. The production of such a crude solution is described, for example, in European patent application EP 1 122 249 A1. As to the term "essentially pure water," reference is made to paragraph 10, page 3 of EP 1 122 249 A1 which is incorporated by reference.

To prepare the hydrogen peroxide which is preferably used, it is possible to employ, for example, the anthraquinone process by means of which virtually the entire world production of hydrogen peroxide is produced. An overview of the anthraquinone process is given in "Ullmann's Encyclopedia of Industrial Chemistry", 5th edition, volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back.

Of course, the preparation of hydrogen peroxide from the elements is also possible. For example, hydrogen peroxide can be produced by reaction of hydrogen and oxygen in the presence of a noble metal catalyst in a liquid reaction medium, whereby the reaction is carried out in the presence of an alkyl sulphate as disclosed in WO 2006/108748. Solutions of hydrogen peroxide in methanol obtained by said method can be used directly for the epoxidation of olefins, in particular in case methanol is employed as preferred solvent such as, e.g., in combination with a TS-1 catalyst or a Ti-MWW catalyst, in particular in combination with a TS-1 catalyst.

Before hydrogen peroxide is used in the process of the invention, it is possible to free, for example, a commercially available hydrogen peroxide solution of undesirable ions. Conceivable methods are, inter alia, those described, for example, in U.S. Pat. No. 5,932,187, DE 42 22 109 A1 or U.S. Pat. No. 5,397,475. It is likewise possible to remove at least one salt present in the hydrogen peroxide solution from the hydrogen peroxide solution by means of ion exchange in an apparatus which contains at least one nonacidic ion exchanger bed having a flow cross-sectional area F and a height H which are such that the height H of the ion exchanger bed is less than or equal to $2.5 \cdot F^{1/2}$, in particular less than or equal to $1.5 \cdot F^{1/2}$. For the purposes of the present invention, it is in principle possible to use all nonacidic ion exchanger beds comprising cation exchangers and/or anion exchangers. It is also possible for cation and anion exchangers to be used as mixed beds within one ion exchanger bed. In a preferred embodiment of the present invention, only one type of nonacidic ion exchangers is used. Further preference is given to the use of basic ion exchange, particularly preferably that of a basic anion exchanger and more particularly preferably that of a weakly basic anion exchanger.

According to the present invention, the standard catalyst load LS of given reactor employed in stage (i) deviates not more than ±5% from the average standard catalyst load LSA, wherein the standard catalyst load LS of a given reactor is that catalyst load which, if constantly applied for a given reaction period T to this reactor containing the catalyst, results in the maximum yield of olefin oxide based on hydroperoxide. Therefore, the standard catalyst load LS for a given reactor relates to a specific set-up which comprises a given reactor, a given catalyst contained in said reactor and a given reaction carried out in this reactor under given reaction conditions such as, e.g., reaction temperature, temperature profile in the reactor, temperature of the cooling medium and its variation during the reaction. Based on these given boundary conditions, the skilled person conducts the reaction in the reactor for a given period T in order to find out which catalyst load is preferred to optimize the overall yield of reaction product. This preliminary test is conducted with reaction conditions which are maintained constant during the given period T. These reaction conditions of the preliminary test are the conditions for the process of the invention. In other words: in preliminary tests, the skilled person determines, for a given reactor Rn and a given set of reaction conditions, including a given catalyst, that catalyst load which, if kept constant, results in an optimized yield of epoxide. These reaction conditions, including the given catalyst, are then applied in the process of the invention, whereas the catalyst load is not kept constant—contrary to the preliminary tests—but adjusted according to prerequisites (3.1), (3.2) and (3.3) as defined above in the context of stage (i).

According to the present invention, the standard catalyst load LS of given reactor employed in stage (i) deviates not more than ±5% from the average standard catalyst load LSA. Therefore, according to a preferred embodiment, the reactors R1, R2, . . . Rn employed in the present invention are essentially identical in terms of the standard catalyst load LS. According to an even more preferred embodiment, each of the reactors R1, R2, . . . Rn contains essentially the same amount of essentially the same catalyst, and the layout of the reactors is essentially identical.

According to the present invention, the catalyst load L is defined as the molar amount of hydroperoxide fed per kilogram catalyst and per hour into a given reactor. The term "catalyst" as used in this context relates to the mass of the catalyst particles employed in the reaction wherein these particles optionally contain, apart from catalytically active material, suitable inert material such as a catalyst support and/or binder material.

In the process of the present invention, at any given point in time, at least one of the at least three reactors R1, R2, . . . Rn is out of operation for regenerating the catalyst present in this at least one reactor so that at least 2 reactors remain in operation.

As far as the regeneration of the at least partially deactivated catalyst contained in the reactor taken out of operation is concerned, no specific limitations exist. Therefore, it is possible to regenerate the catalyst either within the reactor, i.e. without removing the catalyst from the reactor, or to remove the catalyst from the reactor, regenerate it outside the reactor, and to charge the reactor with the regenerated catalyst.

In a preferred process, the catalyst is regenerated by means of a thermal treatment of the catalyst in the presence of a gas stream at above 120° C., preferably above 350° C. and in particular at from 400° C. to 650° C., in the reactor in which the reaction of the olefin had taken place. During the thermal treatment, the mass-based residence time of the gas stream over the catalyst is more than 2 hours, preferably in the range from 3 to 10 hours and particularly preferably in the range from 4 to 6 hours. The regeneration gas generally contains less than 20% by volume, preferably from 0.1 to 10% by volume, in particular from 0.1 to 5% by volume and more preferably from 0.1 to 2% by volume, of oxygen. Preference is given to using a mixture of air and respective volumes of nitrogen. The term "mass-based residence time" used for the purposes of the present invention in the context of regeneration of the catalyst refers to the ratio of the catalyst mass in [kg] divided by the mass flow of the gas in [kg/h] used in the regeneration. In general, the regeneration is carried out so that the pressure drop over the reactor is not more than 4 bar, preferably not more than 3 bar and in particular not more than 2.5 bar. The above-described heating, either in the reactor, for example the tubular reactor, or in an external oven, is preferably carried out at a heating rate of from 0.1 to 20° C./min, preferably from 0.3 to 15° C./min, and in particular from 0.5 to 10° C./min.

According to a further embodiment of the regeneration of process of the present invention, the catalyst can be washed with a suitable solvent in the reactor or in a suitable external apparatus in order to remove desired product which is still adhering, before the heating according to the regeneration procedure. The washing is carried out in a manner such that, although the respective adhering desired products can be removed, temperature and pressure are not chosen to be so high that most organic deposits are likewise removed. Preferably, only washing with a suitable solvent is carried out. Thus, all solvents in which the respective desired product is readily soluble are suitable for this wash process. The amount of solvent used and the duration of the wash process are not critical. The wash process can be repeated several times and can be carried out at elevated temperatures. With the use of $CO_2$ as a solvent, supercritical pressure is preferred; otherwise, the wash process can be effected under normal pressure or elevated pressure or supercritical pressure. After the end of the wash process, drying is generally effected. Although the drying process is in general not critical, the drying temperature should not too greatly exceed the boiling point of the solvent used for the washing, in order to avoid abrupt vaporization of the solvent in the pores, in particular in the micropores of the catalytically active material, in particular the zeolite, since this too may lead to damage to the lattice structure of the catalyst.

In stage (i) of the present process, the reaction is carried out in at least 3 reactors R1, R2, . . . Rn connected in parallel wherein n is the number of reactors and preferably in the range of from 1 to 15. Preferably, n is less or equal to 10, for example less or equal to 9, less or equal to 8, less or equal to 7, less or equal to 6, less or equal to 5, or less or equal to 4. Particularly preferably, n is equal to 4. Therefore, in stage (i) the reaction is preferably carried out in exactly four reactors R1, R2, R3, R4 connected in parallel.

Even more preferably, the reaction in stage (i) is carried out so that at a given point in time, exactly one reactor is taken out of operation for catalyst regeneration, and 3 reactors remain in operation.

According to an especially preferred embodiment of the process of the present invention, the at least 3, more preferably the at least 4 reactors and in particular the exactly 4 reactors R1, R2, . . . Rn are sequentially taken into operation.

If, e.g., the process in stage (i) is carried out using exactly 3 reactors operated in parallel, a first reactor containing fresh or freshly regenerated catalyst is taken into operation. After a certain period of time, when the catalyst of the first reactor begins to deactivate, a second reactor containing fresh or freshly regenerated catalyst is taken into operation. Again, after a certain period of time, the third reactor containing fresh or freshly regenerated catalyst is taken into operation while the first reactor, now containing the most deactivated catalyst, is taken out of operation for regeneration of the catalyst, and the second and the third reactor remain in operation. From that point in time when the first reactor is taken out of operation, the period of time begins encompassing the "given point in time" referred to in feature (2) of the process of the invention.

If, according to an especially preferred embodiment of the present invention, the process in stage (i) is carried out using exactly 4 reactors connected in parallel, a first reactor containing fresh or freshly regenerated catalyst is taken into operation. After a certain period of time, when the catalyst of the first reactor begins to deactivate, a second reactor containing fresh or freshly regenerated catalyst is taken into operation. Again, after a certain period of time, a third reactor containing fresh or freshly regenerated catalyst is taken into operation. After another certain period of time, the fourth reactor containing fresh or freshly regenerated catalyst is taken into operation. Shortly prior to, simultaneously with, or shortly after taking the fourth reactor into operation, the first reactor, now containing the most deactivated catalyst, is taken out of operation for regeneration of the catalyst, and the second, the third and the fourth reactor remain in operation. From that point in time on, when the first reactor is taken out of operation, the period of time begins encompassing the "given point in time" referred to in feature (2) of the process of the invention. After regeneration of the catalyst of the first reactor, the first reactor is taken into operation again, and shortly before or simultaneously, the second reactor now containing the most deactivated catalyst, is taken out of operation.

According to preferred embodiments of the present invention, typical values for LS of a given reactor are in the range of from 7 to 13 mol/kg/h, preferably of from 8 to 12 mol/kg/h and even more preferably of from 9 to 11 mol/kg/h such as, e.g., 9 or 9.5 or 10 or 10.5 or 11 mol/kg/h.

According to the present invention, the catalyst load L of a given reactor at a given point in time is within the range of (0.5-1.5) LS, LS being the standard catalyst load of this reactor. More preferably, the catalyst load of a given reactor is within the range of from (0.55-1.45) LS, more preferably of from (0.6-1.4) LS, more preferably of from (0.65-1.35) LS and even more preferably of from (0.7-1.3) LS.

Moreover, according to the present invention, the catalyst load L of at least one of the reactors in operation deviates more than ±5% from the average standard catalyst load LSA and is different from the catalyst load of each of the other reactors. Thus, the catalyst load L of at least one of the reactors in operation is within the range (1.05 LSA<L≦1.5 LS) or within the range of from (0.5 LS≦L<0.95 LSA). Preferably, the catalyst load L of at least one of the reactors in operation is within the range (1.1-1.5) LS or within the range of from (0.5-0.9) LS, more preferably within the range (1.1-1.4) LS or within the range of from (0.6-0.9) LS, more preferably within the range (1.1-1.35) LS or within the range of from (0.65-0.9) LS, and even more preferably within the range of from (1.1-1.3) LS or within the range of from (0.7-0.9) LS.

Therefore, according to an especially preferred embodiment of the present invention wherein exactly 4 reactors are used and wherein exactly 3 reactors are in operation at a given point in time, one reactor being out of operation, the catalyst load of a first reactor is in the range of from (1.1-1.5) LS1, LS1 being the standard catalyst load of the first reactor, the catalyst load of a second reactor is in the range of from (0.95-1.05) LS2, LS2 being the standard catalyst load of the second reactor, and the catalyst load of the third reactor is in the range of from (0.5-0.9) LS3, LS3 being the standard catalyst load of the third reactor.

According to a further preferred embodiment of the present invention wherein exactly 4 reactors are used and wherein exactly 3 reactors are in operation at a given point in time, one reactor being out of operation, the catalyst load of a first reactor is in the range of from (1.1-1.4) LS1, LS1 being the standard catalyst load of the first reactor, the catalyst load of a second reactor is in the range of from (0.95-1.05) LS2, LS2 being the standard catalyst load of the second reactor, and the catalyst load of the third reactor is in the range of from (0.6-0.9) LS3, LS3 being the standard catalyst load of the third reactor.

According to a further preferred embodiment of the present invention wherein exactly 4 reactors are used and wherein exactly 3 reactors are in operation at a given point in time, one reactor being out of operation, the catalyst load of a first reactor is in the range of from (1.1-1.3) LS1, LS1 being the standard catalyst load of the first reactor, the catalyst load of a second reactor is in the range of from (0.95-1.05) LS2, LS2 being the standard catalyst load of the second reactor, and the catalyst load of the third reactor is in the range of from (0.7-0.9) LS3, LS3 being the standard catalyst load of the third reactor.

Unexpectedly, according to the present invention, it was found that the less deactivated a catalyst is, the higher the catalyst load of the reactor containing this catalyst should be.

Thus, according to a preferred embodiment of the present invention, the catalyst load L of a given reactor is changed from an initial value in the range of from (1.1-1.5) LS, preferably from (1.1-1.4) LS and even more preferably from (1.1-1.3) LS at the beginning of the reaction carried out in this reactor to a value in the range of from (0.95-1.05) LS, preferably from (0.97-1.03) LS, and then to a value in the range of from (0.5-0.9) LS, preferably from (0.6-0.9) LS, even more preferably from (0.7-0.9) LS, before the reactor is taken out of operation for regenerating the catalyst, LS being the standard catalyst load of the reactor.

If, for example, exactly 2 reactor are in operation, the reactor containing the fresh, freshly regenerated or the least deactivated catalyst is operated so that its catalyst load is in the range of from (1.05 LSA<L≦1.5 LS) or in the more preferred ranges thereof, such as from (1.1-1.3) LS, whereas the catalyst load of the other reactor, containing a more deactivated catalyst, is operated so that its catalyst load is either in the range of from (0.95 LSA<L<1.05 LSA), or in the range of from (0.5 LS≦L<0.95 LSA) or in the more preferred ranges thereof, such as (0.7-0.9) LS.

If, according to a preferred embodiment of the present invention, exactly 3 reactors are in operation, it is preferred that, at a given point in time, the reactor containing a fresh, freshly regenerated or the least deactivated catalyst is operated so that its catalyst load is in the range of from (1.05 LSA<L≦1.5 LS) or in the more preferred ranges thereof, such as (1.1-1.3) LS. Even more preferably, the catalyst load of the reactor, containing the most deactivated catalyst, is operated so that its catalyst load is in the range of (0.5 LS≦L<0.95 LSA) or in the more preferred ranges thereof, such as (0.7-0.9) LS. The reactor which contains catalyst exhibiting a medium deactivation degree compared to the catalysts of the other two reactors, is preferably operated so that its catalyst load is within the range of from (0.95-1.05) LS, preferably of from (0.97-1.03) LS.

According to the present invention, a typical period of time for operating a reactor with a catalyst load in the range of from (1.1-1.5) LS, most preferably in the range of from (1.1-1.3) LS, is in the range of from 200 to 400 h, preferably in the range of from 225 to 375 h, and more preferably in the range of from 250 to 350 h. A typical period of time for operating a reactor with a catalyst load in the range of from (0.95-1.05) LS is in the range of from 200 to 400 h, preferably in the range of from 225 to 375 h, and more preferably in the range of from 250 to 350 h. A typical period of time for operating a reactor with a catalyst load in the range of from (0.5-0.9) LS, most preferably in the range of from (0.7-0.9) LS is in the range of from 200 to 400 h, preferably in the range of from 225 to 375 h, and more preferably in the range of from 250 to 350 h.

Therefore, if according to an especially preferred embodiment of the present invention, the process in stage (i) is carried out using exactly 4 reactors connected in parallel and the reactors are sequentially taken into operation, a first reactor containing fresh or freshly regenerated catalyst is taken into operation, its catalyst load being in the range of from (1.05 LSA<L≦1.5 LS1), preferably of from (1.1-1.5) LS1, more preferably of from (1.1-1.4) LS1 and even more preferably of from (1.1-1.3) LS1. After a period of from 200 to 400 h, preferably from 225 to 375 h, and more preferably from 250 to 350 h, when the catalyst of the first reactor begins to deactivate, a second reactor containing fresh or freshly regenerated catalyst is taken into operation, its catalyst load being in the range of from (1.05 LSA<L≦1.5 LS2), preferably of from (1.1-1.5) LS2, more preferably of from (1.1-1.4) LS2 and even more preferably of from (1.1-1.3) LS2. Shortly before, simultaneously to, or shortly after taking the second reactor into operation, the catalyst load of the first reactor is changed to a value in the range of from (0.95 LSA<L<1.05 LSA), preferably of from (0.95-1.05) LS1. After a period of from 200 to 400 h, preferably from 225 to 375 h, and more preferably from 250 to 350 h, when the catalyst of the first reactor exhibits an even more increased degree of deactivation and the second reactor begins to deactivate, a third reactor containing fresh or freshly regenerated catalyst is taken into operation, its catalyst load being in the range of from (1.05 LSA<L≦1.5 LS3), preferably of from (1.1-1.5) LS3, more preferably of from (1.1-1.4) LS3 and even more preferably of from (1.1-1.3) LS3. Shortly before, simultaneously to, or shortly after taking the third reactor into operation, the catalyst load of the second reactor is changed to a value in the range of from (0.95 LSA<L<1.05 LSA), preferably of from (0.95-1.05) LS2, and the catalyst load of the first reactor is changed to a value in the range of from (0.5 LS1<L≦0.95 LSA), preferably of from (0.5-0.9) LS1, more preferably of from (0.6-0.9) LS1 and even more preferably of from (0.7-0.9) LS1. Again, after a period of from 200 to 400 h, preferably from 225 to 375 h, and more preferably from 250 to 350 h, when the catalyst of the first reactor exhibits an even more increased degree of deactivation, resulting in olefin oxide yields obtained from the first reactor which no longer meet the requirements of the process, the second reactor exhibits an increased degree of deactivation, and the catalyst of the third reactor begins to deactivate, a fourth reactor containing fresh or freshly regenerated catalyst is taken into operation, its catalyst load being in the range of from (1.05 LSA<L≦1.5 LS4), preferably of from (1.1-1.5) LS4, more preferably of from (1.1-1.4) LS4 and even more preferably of from (1.1-1.3) LS4. Shortly before, simultaneously to, or shortly after taking the fourth reactor into operation, the catalyst load of the third reactor is changed to a value in the range of from (0.95 LSA<L<1.05 LSA), preferably of from (0.95-1.05) LS3, and the catalyst load of the second reactor is changed to a value in the range of from (0.5 LS2<L≦0.95 LSA), preferably of from (0.5-0.9) LS2, more preferably of from (0.6-0.9) LS2 and even more preferably of from (0.7-0.9) LS2, whereas the first reactor is taken out of operation for regeneration of the catalyst. Thenceforward, when the first reactor is taken out of operation, that period of time begins which encompasses the "given point in time" referred to in feature (2) of the process of the invention.

Exemplary, for above-described preferred embodiment, the further continuous process according to the invention and starting with taking the first reactor out of operation shall be described in more detail.

Once the first reactor is taken out of operation for regeneration of the deactivated catalyst, 3 reactors remain in operation. Preferably, after a period of from 200 to 400 h, preferably from 225 to 375 h, and more preferably from 250 to 350 h, the catalyst present in the second reactor exhibits a degree of deactivation resulting in olefin oxide yields obtained from the second reactor which no longer meets the requirements of the process. At this point in time, the second reactor is taken out of operation and, shortly before, simultaneously to, or shortly after taking the second reactor out of operation, the first reactor containing the freshly regenerated catalyst, is taken into operation. Thenceforward, the first reactor is operated of from 200 to 400 h, preferably from 225 to 375 h, and more preferably from 250 to 350 h at a catalyst load of from (1.05 LSA<L≦1.5 LS1), preferably of from (1.1-1.5) LS1, more preferably of from (1.1-1.4) LS1 and even more preferably of from (1.1-1.3) LS1. The third reactor is now operated at a catalyst load of from (0.5 LS3<L≦0.95 LSA), preferably of from (0.5-0.9) LS3, more preferably of from (0.6-0.9) LS3 and even more preferably of from (0.7-0.9) LS3, whereas the fourth reactor is operated at a catalyst load of from (0.95 LSA<L<1.05 LSA), preferably of from (0.95-1.05) LS4. Then, after a period of from 200 to 400 h, preferably from 225 to 375 h, and more preferably from 250 to 350 h, the catalyst of the third reactor will exhibit a degree of deactivation resulting in olefin oxide yields obtained from the third reactor which no longer meets the requirements of the process. Therefore, after this period, the third reactor R3 will be taken out of operation, the catalyst loads of the reactor R1 and R4 will be decreased according to the invention, and reactor R2 containing freshly regenerated catalyst will be taken into operation. This sequence of taking reactors out of and into operation will then continue accordingly. If necessary, for example after several regeneration cycles, a catalyst of a given reactor can be at least partially or completely replaced by fresh catalyst.

According to the present invention, requirement (2) of the novel process according to which, at any given point in time, at least one reactor is out of operation has to be understood in such a way that there are short periods wherein one reactor is taken out of operation and another reactor is taken into operation and wherein it is possible that according to, for example, process safety requirements or the like, there may be a short overlap so that the reactor to be taken out of operation is still in operation whereas the reactor to be taken into operation is already in operation. These short periods which are generally in the order of not more than 5 hours, preferably less than 5 h such as, e.g., 1 to 4 h, and which, due to specific technical demands of the overall process, represent an exemption of the general rule that at least one reactor is out of operation, shall not contribute to the requirement (2) of the present invention.

According to the present invention, all ranges disclosed above have to be chosen so that the average catalyst load LA which is defined as the sum of the catalyst loads of the reactors in operation at the respective point in time divided by the number of these reactors is in the range of from (0.8-1.2) LSA. More preferably, the average catalyst load LA is in the range of from (0.85-1.15) LSA, even more preferably in the range of from (0.9-1.1) LSA. Especially for the continuous process of the present invention, it was found that this requirement considerably facilitates the overall apparatus set-up since, due to the fact that the average catalyst load is in a comparatively narrow range, the combined effluents from the reactors R1, R2, . . . Rn and thus the product stream obtained from (i) are/is also constantly in a narrow range. This specific choice of the average catalyst load redundantizes any means which might be necessary to handle strongly fluctuating flows leaving stage (i) of the process.

Therefore, the novel process according to the present invention combines the advantage that the deactivation of the catalysts present in the reactors in operation is compensated to a certain degree by respectively adapting the catalyst load, with an efficient limitation of the variation of the effluent flow from the reactors, thus minimizing the apparatus requirements.

Stage (a) of the process according to the present invention comprises reaction stage (i). The effluents obtained from the reactors in operation and employed in stage (i) are preferably collected and combined to one overall effluent stream.

The reaction in the at least 3 reactors R1, R2, . . . Rn according to stage (i) is preferably carried out at reaction conditions such that the overall hydroperoxide conversion, preferably the overall hydrogen peroxide conversion, is at least 80%, more preferably at least 85% and still more preferably at least 90%, such as 90%, 91%, 92%, 93%, 94%, 95%, 96%, 97% 98%, to or 99%. Furthermore, the overall yield in olefin oxide, based on hydrogen peroxide, is preferably at least 80%, more preferably at least 85%, even more preferably at least 86% and in particular at least 87%.

According to especially preferred embodiment, the pressure in the reactors is preferably in the range of from 10 to 30 bar, more preferably from 15 to 25 bar, and the inlet temperature of the cooling water, optionally used for at least partially removing heat generated during epoxidation, is in the range of preferably from 20 to 70° C., more preferably from 25 to 65° C. and particularly preferably from 30 to 60° C.

According to a preferred embodiment of the invention according to which the reactors in stage (i) are fixed-bed reactors, the respective product mixture obtained therefrom, and the overall effluent consisting of the combined reactor effluents, essentially consists of olefin oxide, preferably propylene oxide, unreacted olefin, preferably propene, optionally solvent, preferably methanol, water, and unreacted hydroperoxide, preferably hydrogen peroxide.

According to a preferred embodiment, the overall effluent obtained from stage (i) has a solvent, preferably methanol content in the range of from 55 to 75 wt.-%, especially preferably of from 60 to 70 wt.-%, based on the total weight of the overall effluent, a water content in the range of from 5 to 25 wt.-%, especially preferably of from 10 to 20 wt.-%, based on the total weight of the overall effluent, an olefin oxide content in the range of from 5 to 20 wt.-%, especially preferably of from 8 to 15 wt.-%, based on the total weight of the overall effluent, and an olefin content in the range of from 1 to 10 wt.-%, especially preferably of from 1 to 5 wt.-%, based on the total weight of the overall effluent.

The temperature of the overall effluent obtained from stage (i) is preferably in the range of from 40 to 70° C., more preferably of from 45 to 65° C. Prior to being fed to the distillation column of (ii), which is described as a preferred embodiment of the present invention below, the overall effluent is preferably heated up in at least one heat exchanger to a temperature in the range of from 55 to 80° C., more preferably of from 60 to 75° C.

Stage (a) can comprise further stages, in particular further reaction stages, intermediate treatment stages, or the like. In a preferred embodiment, stage (a) comprises at least two reaction stages. More preferably, stage (a) consists of two reaction stages. Even more preferably, stage (a) comprises at least one intermediate treatment stage, more preferably at least one intermediate separation stage. In particular, stage (a) comprises exactly one intermediate separation stage.

Therefore, the present invention also relates to a process wherein stage (a) comprises (i) reaction of the olefin, preferably propene, with a hydroperoxide, preferably hydrogen peroxide, to give a mixture comprising olefin oxide, preferably propylene oxide, unreacted olefin, preferably propene, and unreacted hydroperoxide, preferably hydrogen peroxide;
(ii) separation of the unreacted olefin, preferably propene, from the mixture resulting from stage (i), obtaining a mixture comprising unreacted hydroperoxide, preferably hydrogen peroxide;
(iii) reaction of the hydroperoxide, preferably hydrogen peroxide, which has been separated off in stage (ii) with olefin, preferably propene.

The term "mixture resulting from stage (i)" as used in the context of the present invention relates to the overall effluent stream comprised of the effluents obtained from those of the at least 3 reactors R1, R2, . . . Rn which are in operation.

In the process according to the invention, it is possible to use the same or different types of reactors in stages (i) and (iii). Thus, it is possible to carry out stage (iii) independently of the reactors used in stage (i), in an isothermal or adiabatic reactor. The term "reactor" as used with respect to stage (iii) comprises a single reactor, a cascade of at least two serially connected reactors, at least two reactors which are operated in parallel, or a multitude of reactors wherein at least two reactors are serially coupled and wherein at least two reactors are operated in parallel. According to a preferred embodiment and apart from the isothermal or adiabatic reactor, stage (iii) can comprise at least one additional reactor which is arranged, for example, as parallel reactor. Preferably, at least one of the additional reactors is operated if, for example, the reactor of stage (iii) is taken out of operation for regeneration purposes concerning the catalyst used. According to one embodiment of stage (iii) of the present invention, stage (iii) consists of two reactors arranged as parallel reactors wherein one reactor is used for carrying out the reaction, and wherein in case this reactor has to be taken out of service, for example due to regeneration purposes, the other reactor is taken into service, thus allowing for carrying out the reaction without interruption of the overall process.

Each of the reactors described above for the reaction according to stage (iii), especially the reactors according to the preferred embodiment, can be operated in downflow or in upflow operation mode. In case the reactors are operated in downflow mode, it is preferred to use fixed-bed reactors which are preferably shaft, tubular, multi-tubular or multi-plate reactors, most preferably equipped with at least one cooling jacket, in case the reactor is designed as isothermic reactor. In case of downflow operation of the reactors, it is possible to choose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydroperoxide rich phase, preferably a hydrogen peroxide rich phase, containing solvent, preferably methanol, and a liquid organic olefin rich phase, preferably a propene rich phase. According to the present invention it is also possible to operate the reaction in downflow and trickle bed mode. In case the reactors are operated in upflow mode, it is preferred to use fixed-bed reactors, in particular shaft reactors.

In stage (iii), particular preference is given to using a shaft reactor, more preferably a continuously operated shaft reactor and particularly preferably a continuously operated, adiabatic shaft reactor.

Therefore, the present invention also relates to a process as described above wherein in stage (i), at least 3 shell-and-tube reactors each having of from 1 to 20,000 internal tubes and being continuously operated in upflow mode, said reactors being operated in parallel, are employed, and wherein in stage (iii), an adiabatic shaft reactor being continuously operated in upflow mode, is employed. Still more preferably, the reaction in the at least three reactors of stage (i) and still more preferably in all reactors used in stages (i) and (iii) is conducted such that in the respective reactor, a single liquid phase is present. Even more preferably, in each of the reactors used in stages (i) and (iii), the catalyst used for the epoxidation reaction is employed as fixed-bed reactor wherein the catalyst is a titanium zeolite catalyst, more preferably a TS-1 or Ti-MWW catalyst and even more preferably a TS-1 catalyst.

According to stage (ii), unreacted olefin is separated from the overall effluent resulting from stage (i). This separation is preferably carried out by distillation using at least one distillation column. The reaction mixture obtained from the at least one reactor, preferably from the at least three reactors used in stage (i), comprising unreacted olefin, olefin oxide, solvent, preferably methanol, water and unreacted hydroperoxide, preferably hydrogen peroxide, is introduced in the distillation column. The distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. According to an especially preferred embodiment, the distillation column has from 5 to 60, preferably from 10 to 50 and especially preferably from 15 to 40 theoretical stages.

According to a still further preferred embodiment, the reaction mixture obtained from (i) is fed to the distillation column of (ii) from 2 to 30 theoretical stages below the top, preferably from 10 to 20 theoretical stages below the top of the column.

At the top of the distillation column of (ii), a stream essentially consisting of olefin oxide, preferably propylene oxide, solvent, preferably methanol and unreacted olefin, preferably propene, is obtained. At the top of the column, preferably a mixture is obtained having a water content of not more than 0.5 wt.-%, preferably of not more than 0.4 wt.-% and still more preferably of not more than 0.3 wt.-%, and having a hydroperoxide, preferably hydrogen peroxide content of not more than 100 ppm, preferably of not more than 20 ppm and still more preferably of not more than 10 ppm, in each case based on the total weight of the mixture obtained at the top of the column.

At the bottom of the distillation column, a stream essentially consisting of solvent, preferably methanol, water and unreacted hydroperoxide, preferably unreacted hydrogen peroxide is obtained. At the bottom of the column, a mixture is obtained having an olefin, preferably a propene content of not more than 50 ppm, preferably of not more than 10 ppm and still more preferably of not more than 5 ppm, and having a olefin oxide, preferably a propylene oxide content of not more than 50 ppm, preferably of not more than 20 ppm and still more preferably of not more than 10 ppm, in each case based on the total weight of the mixture obtained at the bottom of the column.

Therefore, depending on the respective point of view, distillative separation according to stage (ii) can be described as separation of unreacted olefin or, alternatively, as separation of olefin oxide.

According to a still further preferred embodiment, the distillation column used in (ii) is configured as dividing wall column having at least one side-offtake, preferably one side-offtake. Preferably, the dividing wall column preferably has from 20 to 60, more preferably from 30 to 50 theoretical stages.

The upper combined region of the inflow and offtake part of the dividing wall column preferably has from 5 to 50%, more preferably from 15 to 30%, of the total number of theoretical stages in the column, the enrichment section of the inflow part preferably has from 5 to 50%, more preferably from 15 to 30%, the stripping section of the inflow part preferably has from 15 to 70%, more preferably from 20 to 60%, the stripping section of the offtake part preferably has from 5 to 50%, more preferably from 15 to 30%, the enrichment section of the offtake part preferably has from 15 to 70%, more preferably from 20 to 60%, and the lower combined region of the inflow and offtake part of the column preferably has from 5 to 50%, more preferably from 15 to 30%, in each case of the total number of theoretical stages in the column.

It is likewise advantageous for the inlet via which the product mixture obtained from (i) is fed into the column and the side offtake via which a part of the solvent, preferably methanol, preferably of from 0 to 50%, more preferably of from 1 to 40%, still more preferably of from 5 to 30% and especially preferably of from 10 to 25% of the total solvent, preferably methanol, is taken off as intermediate boiler and, still more preferably, directly fed back to stage (i), to be arranged at different heights in the column relative to the position of the theoretical stages. The inlet is preferably located at a position which is from 1 to 25, more preferably from 5 to 15 theoretical stages above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical stage.

In the abovementioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

The differential pressure over the dividing wall column can be utilized as regulating parameter for the heating power. The distillation is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar.

The distillation is then preferably carried out in a temperature range from 65 to 100° C., more preferably from 70 to 85° C. The distillation temperature is measured at the bottom of the tower.

In case such a divided wall column is used, at the top of the distillation column of (ii), a stream essentially consisting of olefin oxide, preferably propylene oxide, solvent, preferably methanol and unreacted olefin, preferably propene, is obtained. At the top of the column, a mixture is obtained having a water content of not more than 500 ppm, preferably of not more than 400 ppm, and still more preferably of not more than 300 ppm, and having a hydroperoxide, preferably hydrogen peroxide content of not more than 50 ppm, preferably of not more than 20 ppm and still more preferably of not more than 10 ppm, in each case based on the total weight of the mixture obtained at the top of the column. Furthermore, the top stream obtained has an olefin, preferably a propene content of from 15 to 35 wt.-%, preferably of from 20 to 30 wt.-% and still more preferably of from 20 to 25 wt.-%, an olefin oxide, preferably a propylene oxide content of from 50 to 80 wt.-%, preferably of from 55 to 75 wt.-% and especially preferably of from 60 to 70 wt.-%, and a solvent, preferably methanol content of from 5 to 20 wt.-%, more preferably of from 7.5 to 17.5 wt.-% and especially preferably of from 10 to 15 wt.-%, in each case based on the total weight of the top stream. The top stream is preferably obtained as a vapour stream.

The stream obtained at the side-offtake of the column can be a vapour or a liquid stream, preferably a liquid stream. At the side-offtake of the distillation column, a stream essentially consisting of solvent, preferably methanol and water is obtained. At the side-offtake of the column, a mixture is obtained having a solvent, preferably a methanol content of at least 90 wt.-%, for example at least 95 wt.-%, preferably at least 96 wt.-% and still more preferably at least 97 wt.-%, and having a water content of not more than 5 wt.-%, preferably of not more than 3.5 wt.-% and still more preferably of not more than 2 wt.-%, in each case based on the total weight of the mixture obtained at the side-offtake of the column.

At the bottom of the distillation column, a stream essentially consisting of solvent, preferably methanol, water and unreacted hydroperoxide, preferably hydrogen peroxide is obtained. At the bottom of the column, a mixture is obtained having an olefin, preferably a propene content of not more than 50 ppm, preferably of not more than 10 ppm and still more preferably of not more than 5 ppm, and having a olefin oxide, preferably a propylene oxide content of not more than 50 ppm, preferably of not more than 20 ppm and still more preferably of not more than 10 ppm, in each case based on the total weight of the mixture obtained at the bottom of the column.

At least part of the stream taken from the side of the dividing wall column can be recycled as solvent into stage (i) of the inventive process. Preferably, at least 90%, more preferably at least 95% of the stream taken from the side-offtake are recycled into stage (i).

The bottoms stream taken from the distillation column, preferably the dividing wall distillation column, essentially consisting of solvent, preferably methanol, water and unreacted hydroperoxide, preferably hydrogen peroxide, is then fed to the reactor of stage (iii). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Still more preferably, fresh olefin, preferably propene, is additionally added directly into the reactor of stage (iii) or added to the bottoms stream obtained from (ii) prior to introducing same into the reactor of stage (iii). Alternatively or additionally, fresh hydroperoxide, preferably hydrogen peroxide can be added.

The selectivity of this reaction in stage (iii) in respect of hydroperoxide, preferably hydrogen peroxide is preferably in the range from 64 to 99%, more preferably in the range from 72 to 90% and particularly preferably in the range from 75 to 87%.

The selectivity of the overall process with stages (i) to (iii) in respect of hydroperoxide, preferably hydrogen peroxide is preferably in the range from 78 to 99%, more preferably in the range from 88 to 97% and particularly preferably in the range from 90 to 96%.

The total hydroperoxide, preferably hydrogen peroxide conversion is preferably at least 99.5%, more preferably at least 99.6%, more preferably at least 99.7% and particularly preferably at least 99.8%.

The reaction mixture obtained from stage (iii) preferably has a solvent content, preferably a methanol content of from 50 to 90 wt.-%, more preferably of from 60 to 85 wt.-% and especially preferably of from 70 to 80 wt.-%, based on the total weight of the reaction mixture. The water content is preferably in the range of from 5 to 45 wt.-%, more preferably of from 10 to 35 wt.-% and especially preferably of from 15 to 25 wt.-%, based on the total weight of the reaction mixture. The olefin oxide, preferably the propylene oxide content, is preferably in the range of from 1 to 5 wt.-%, more preferably of from 1 to 4 wt.-% and especially preferably of from 1 to 3 wt.-%, based on the total weight of the reaction mixture. The olefin, preferably the propene content is preferably in the range of from 0 to 5 wt.-%, more preferably of from 0 to 3 wt.-% and especially preferably of from 0 to 1 wt.-%, based on the total weight of the reaction mixture.

The process according to the present invention can comprise further stages, for example stages (b), (c), and (d). The process according to the present invention can comprise stage (a) and stage (b) or stage (a), stage (b) and stage (c) or stage (a), stage (b), stage (c) and stage (d):

(b) separating unreacted olefin from the mixture (Ma) by distillation to obtain a mixture (M-bi) comprising at least 80 wt.-% of olefin and a mixture (M-bii) comprising solvent, preferably methanol, water and at least 7 wt.-% of olefin oxide;

(c) separating olefin oxide from the mixture (M-bii) in at least one distillation stage to obtain a mixture (M-ci) comprising at least 99 wt.-% of olefin oxide and a mixture (M-cii) comprising water and at least 55 wt.-% of solvent, preferably methanol;

(d) separating solvent, preferably methanol from the mixture (M-cii) in at least one distillation stage to obtain a mixture (M-di) comprising at least 85 wt.-% of solvent, preferably methanol and up to 10 wt.-% of water, and a mixture (M-dii) comprising at least 90 wt.-% of water.

Stage (b)

According to stage (b), unreacted olefin is separated from the mixture (M-a) by distillation to obtain a mixture (M-bi) comprising at least 80 wt.-% of olefin and a mixture (M-bii) comprising solvent, preferably methanol, water and at least 7 wt.-% of olefin oxide.

In case chemical grade propene is used as starting material of stage (a), the mixture (M-bi) can additionally comprise up to 15 wt.-%, preferably of from 5 to 10 wt.-% of propane, based on the total weight of mixture (M-bi).

Separation according to stage (b) is preferably carried out in at least one distillation column, more preferably in one distillation column. Preferably, this column has of from 5 to 40, more preferably of from 10 to 35 and especially preferably of from 15 to 30 theoretical stages.

The distillation column is preferably operated at a top pressure of from 1 to 5 bar, more preferably of from 1 to 4 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar.

According to a still further preferred embodiment, a mixture (M-bi) is obtained at the top of the distillation column comprising at least 85 wt.-% of olefin, still more preferably of from 85 to 90 wt.-% of olefin, preferably of propene.

Preferably, the mixture (M-bii) obtained as bottoms stream comprises of from 55 to 80 wt.-%, more preferably from 60 to 75 wt.-% and especially preferably from 65 to 70 wt.-% of solvent, preferably methanol, of from 13 to 25 wt.-%, more preferably from 15 to 20 wt.-% of water, and at least 7 wt.-%, more preferably at least 8 wt.-%, more preferably at least 9 wt.-% and especially preferably at least 10 wt.-%, for example from 10 to 15 wt.-% such as about 10, about 11, about 12, about 13, about 14 or about 15 wt.-% of olefin oxide, preferably propylene oxide.

Stage (c)

According to stage (c), mixture (M-bii) obtained from stage (b) as bottoms stream is subjected to a further distillative separation process in which a mixture (M-ci) comprising at least 99 wt.-% of olefin oxide and a mixture (M-cii) comprising water and at least 55 wt.-% of solvent, preferably methanol are obtained.

Separation according to stage (c) is preferably carried out in at least one distillation column, more preferably in one distillation column. Preferably, this column has of from 30 to 110, more preferably of from 40 to 100 and especially preferably of from 50 to 90 theoretical stages.

The distillation column is preferably operated at a top pressure of from 1 bar or less. Especially preferably, the distillation column is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

According to a preferred embodiment of the inventive process, the mixture (M-ci) obtained as top stream comprises at least 99.1 wt.-%, more preferably at least 99.2 wt.-%, more preferably at least 99.3 wt.-%, more preferably at least 99.4 wt.-%, and still more preferably at least 99.5 wt.-% of olefin oxide, preferably propylene oxide. Preferred contents of (M-ci) with respect to olefin oxide are, for example, in the range of from 99.1 to 99.9, more preferably from 99.2 to 99.9, more preferably from 99.3 to 99.9, more preferably from 99.4 to 99.9 and still more preferably from 99.5 to 99.9 wt.-%, based on the total weight of mixture (M-ci).

According to a preferred embodiment of the inventive process, the mixture (M-cii) obtained as bottoms stream comprises of from 55 to 85 wt.-%, more preferably from 65 to 80 wt.-% and especially preferably from 75 to 80 wt.-% of solvent, preferably methanol, and of from 15 to 45 wt.-%, more preferably from 20 to 35 wt.-% and especially preferably of from 20 to 25 wt.-% of water, wherein the content of mixture (M-cii) regarding solvent, preferably methanol as well as water is higher than the respective content of mixture (M-bii).

According to a further embodiment of the present invention, separation of olefin oxide, preferably propylene oxide, in stage (c) is performed in at least two, more preferably in two distillation columns.

Still more preferably, the olefin oxide stream obtained from the second distillation column comprises at least 99.9 wt.-% of olefin oxide, still more preferably at least 99.99 wt.-% of olefin oxide.

Preferably, the first column has of from 30 to 110, more preferably of from 40 to 100 and especially preferably of from 50 to 90 theoretical stages.

The first column is preferably operated at a top pressure of from 1 bar or less. Especially preferably, the distillation column is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

Preferably, the second column has of from 25 to 60, more preferably of from 30 to 55 and especially preferably of from 35 to 50 theoretical stages.

The second column is preferably operated at a top pressure of from 1 to 7 bar, more preferably from 2 to 6 bar and especially preferably from 3 to 5 bar.

The mixture obtained from the top of the first column which is fed as feed stream to the second column can further contain certain by-products resulting from one or more stages of the overall epoxidation process, having boiling points lower than the olefin oxide, preferably the propylene oxide. Examples for such by-products are aldehydes such as, for example, acetaldehyde and/or formaldehyde. These by-products can be contained in the top stream of the first column in an amount of up to 0.3 wt.-%, preferably up to 0.20 wt.-% and especially preferably up to 0.15 wt.-%, based on the total weight of (M-cii) and referring to the sum of the respective weights of these low-boiling compounds.

Stage (d)

According to stage (d), mixture (M-cii) obtained from stage (c) as bottoms stream is subjected to a further distillative separation process in which a mixture (M-di) comprising at least 85 wt.-% of solvent, preferably methanol and up to 10 wt.-% of water, and a mixture (M-dii) comprising at least 90 wt.-% of water are obtained.

Distillation in stage (d) can be performed in one, two, three or more distillation columns.

According to one aspect of the present invention, distillation in stage (d) is carried out in one distillation column. Preferably, this distillation column has of from 10 to 100, more preferably of from 20 to 90 and especially preferably of from 30 to 70 theoretical stages.

The distillation column is operated at a pressure preferably of from 1 to 12 bar, more preferably of from 2 to 11 bar and especially preferably of from 3 to 10 bar.

The mixture (M-di) obtained from the top of the column comprises at least 85 wt.-% of solvent, preferably methanol and up to 10 wt.-% of water, more preferably at least 90 wt.-% of solvent, preferably methanol and up to 10 wt.-% of water, more preferably at least 95 wt.-% of solvent, preferably methanol and up to 5 wt.-% of water, more preferably at least 96 wt.-% of solvent, preferably methanol and up to 4 wt.-% of water and especially preferably at least 97 wt.-% of solvent, preferably methanol and up to 3 wt.-% of water.

The reflux ratio of this column is preferably in the range of 1 to 10, more preferably in the range of 2 to 8.

According to a preferred embodiment of the present invention, distillation in stage (d) is performed in a two-pressure distillation process, where in a first distillation column (K1), distillation is carried out at a top pressure which is different from the top pressure of a second distillation column (K2).

The term "first column (K1)" as used in the context of the present invention relates to the column into which the mixture (M-cii) is fed. The term "second column (K2)" as used in the context of the present invention relates to the column into which the bottoms stream obtained from (K1) is fed.

The distillation in the first column (K1) is preferably carried out at a top pressure in the range of from 2 to 8 bar, more preferably of from 2 to 6 bar and especially preferably in the range of from 2.5 to 6 bar. The distillation in the second column (K2) is preferably carried out at a top pressure in the range from 8 to 15 bar, more preferably of from 8.5 to 14 bar, and especially preferably in the range from 9 to 13 bar.

Distillation column (K1) has preferably of from 5 to 30, more preferably from 7 to 25 and especially preferably of from 10 to 20 theoretical stages.

Distillation column (K2) has preferably of from 5 to 60, more preferably from 10 to 55 and especially preferably of from 15 to 50 theoretical stages.

The top stream (M-di) obtained from column (K2) comprises at least 85 wt.-% of solvent, preferably methanol and up to 10 wt.-% of water, more preferably at least 90 wt.-% of solvent, preferably methanol and up to 10 wt.-% of water, more preferably at least 95 wt.-% of solvent, preferably methanol and up to 5 wt.-% of water, more preferably at least 96 wt.-% of solvent, preferably methanol and up to 4 wt.-% of water and especially preferably at least 97 wt.-% of solvent, preferably methanol and up to 3 wt.-% of water. According to particularly preferred embodiment, the top stream obtained from column (K2) comprises less than 3 wt.-% of water such as, for example, from 1 to 2 wt.-% of water.

The mixture (M-dii) obtained from the bottom of column (K2) comprises at least 90 wt.-% of water, more preferably at least 95 wt.-% of water and especially preferably at least 97 wt.-% of water. Preferably (M-dii) is essentially free of solvent, preferably methanol, i.e. it has a solvent, preferably methanol content of less than 5 ppm, more preferably of less than 1 ppm. In addition to water, (M-dii) can comprise certain by-products resulting from one or more stages of the overall epoxidation process. Examples for such by-products are glycol compounds such as propylene glycols. These by-products can be contained in (M-dii) in an amount of up to 4 wt.-%, preferably up to 3 wt.-%.

Additionally, the process of the present invention can comprise further stages, for example purification stages as far as olefin oxide or valuable products are concerned.

The invention claimed is:

1. A continuous process for the preparation of an olefin oxide comprising a stage (a)
   (a) reacting an olefin with a hydroperoxide in the presence of a catalyst to obtain a mixture (Ma) comprising olefin oxide,
   wherein stage (a) comprises at least one reaction stage (i) wherein in (i)
   (1) the reaction is carried out in at least 3 reactors R1, R2, . . . Rn connected in parallel, wherein each reactor contains the catalyst and wherein the standard catalyst load LS of a given reactor deviates not more than ±5% from the average standard catalyst load LSA;
   (2) at any given point in time during carrying out the reaction, at least one of the at least 3 reactors R1, R2, . . . Rn is out of operation for regenerating the catalyst present in this at least one reactor so that at least 2 reactors remain in operation; and
   (3) at this point in time, the at least 2 reactors in operation are operated so that
      (3.1) the average catalyst load LA is in the range of from (0.8-1.2) LSA;
      (3.2) the catalyst load L of a given reactor is within the range of (0.5-1.5) LS, LS being the standard catalyst load of this reactor; and
      (3.3) the catalyst load L of at least one of these reactors deviates more than ±5% from the average standard catalyst load LSA and is different from the catalyst load of each of the other reactors;
   wherein the catalyst load L of a given reactor is the molar amount of hydroperoxide fed per kilogram catalyst and per hour into this reactor;
   wherein the standard catalyst load LS of a given reactor is the catalyst load which, if constantly applied for a given reaction period T to this reactor containing the catalyst, results in the maximum yield of olefin oxide based on hydroperoxide;
   wherein the average standard catalyst load LSA is the sum of the standard catalyst loads of all reactors R1, R2, . . . Rn divided by n;
   and wherein the average catalyst load LA at a given point in time is the sum of the catalyst loads of the reactors in operation at this point in time divided by the number of these reactors, wherein n is the number of reactors.

2. The process of claim 1, wherein the hydroperoxide is hydrogen peroxide.

3. The process of claim 1, wherein the catalyst is a titanium zeolite catalyst.

4. The process of claim 1, wherein the olefin is propene.

5. The process of claim 1, wherein in (i), the olefin is reacted in the presence of a solvent.

6. The process of claim 5, wherein the solvent is methanol.

7. The process of claim 1, wherein the at least 3 reactors R1, R2, . . . Rn are shell-and-tube reactors and the catalyst present therein is a fixed-bed catalyst.

8. The process of claim 1, wherein according to (3.2), the catalyst load L of a given reactor is within the range of from (0.7-1.3) LS, LS being the standard catalyst load of this reactor.

9. The process of claim 1, wherein according to (3.1), the average catalyst load LA is in the range of from (0.9-1.1) LSA.

10. The process of claim 1, wherein n is less than or equal to 10.

11. The process of claim 10, wherein n is 4.

12. The process of claim 11, wherein in (i), at any given point in time, 1 reactor is out of operation and 3 reactors are in operation.

13. The process of claim 12, wherein at this point in time, the catalyst load of a first reactor is in the range of from (1.1-1.5) LS1, LS1 being the standard catalyst load of the first reactor, the catalyst load of a second reactor is in the range of from (0.95-1.05) LS2, LS2 being the standard catalyst load of the second reactor, and the catalyst load of the third reactor is in the range of from (0.5-0.9) LS3, LS3 being the standard catalyst load of the third reactor.

14. The process of claim 12, wherein at this point in time, the catalyst load of a first reactor is in the range of from (1.1-1.3) LS1, LS1 being the standard catalyst load of the first reactor, the catalyst load of a second reactor is in the range of from (0.95-1.05) LS2, LS2 being the standard catalyst load of the second reactor, and the catalyst load of the third reactor is in the range of from (0.7-0.9) LS3, LS3 being the standard catalyst load of the third reactor.

15. The process of claim 1, wherein the standard catalyst load LS of a given reactor is in the range of from 7 to 13 mol/kg(catalyst)/h.

16. The process of claim 1, wherein in a given reactor, the catalyst load L is changed stepwise during the reaction in this reactor.

17. The process of claim 16, wherein the catalyst load L is changed from an initial value in the range of from (1.1-1.5) LS at the beginning of the reaction to a value in the range of from (0.95-1.05) LS and then to a value in the range of from (0.5-0.9) LS before the reactor is taken out of operation for regenerating the catalyst, LS being the standard catalyst load of the reactor.

18. The process of claim 17, the hydroperoxide being hydrogen peroxide, the solvent being methanol, the catalyst being a titanium silicalite catalyst and the olefin being propene, wherein the standard catalyst load LS of the reactor is in the range of from 7 to 13 mol/kg(catalyst)/h and wherein a catalyst load L in the range of from (1.1-1.3) LS is maintained for a period in the range of from 250 to 350 h, a catalyst load L in the range of from (0.95-1.05) LS is maintained for a period in the range of from 250 to 350 h and a catalyst load L in the range of from (0.7-0.9) LS is maintained for a period in the range of from 250 to 350 h.

19. The process of claim 1, wherein the at least 3 reactors R1, R2, . . . Rn reactors are taken into operation sequentially.

20. The process of claim 1, wherein in (i), a mixture is obtained which comprises olefin oxide, unreacted olefin and unreacted hydroperoxide, and wherein stage (a) additionally comprises
   (ii) separation of the unreacted olefin from the mixture resulting from stage (i), obtaining a mixture comprising unreacted hydroperoxide;
   (iii) reaction of the hydroperoxide which has been separated off in stage (ii) with olefin.

* * * * *